US011426276B2

(12) United States Patent
Tran et al.

(10) Patent No.: US 11,426,276 B2
(45) Date of Patent: Aug. 30, 2022

(54) STENTED PROSTHETIC HEART VALVE DELIVERY SYSTEM HAVING AN EXPANDABLE BUMPER

(71) Applicant: Medtronic Vascular, Inc., Santa Rosa, CA (US)

(72) Inventors: Don Tran, Novato, CA (US); Martha Barajas-Torres, Santa Rosa, CA (US); James Mitchell, Windsor, CA (US); Leonel Mendoza, Santa Rosa, CA (US); Siyan Som, Fulton, CA (US); Jill Mendelson, San Francisco, CA (US); David Grossman, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 788 days.

(21) Appl. No.: 15/291,389

(22) Filed: Oct. 12, 2016

(65) Prior Publication Data
US 2018/0098848 A1    Apr. 12, 2018

(51) Int. Cl.
*A61F 2/24*     (2006.01)
(52) U.S. Cl.
CPC .......... *A61F 2/2436* (2013.01); *A61F 2/2418* (2013.01)
(58) Field of Classification Search
CPC .... A61F 2/95; A61F 2/966; A61F 2002/9665; A61F 2002/9522; A61F 2002/9511;
(Continued)

(56) References Cited

U.S. PATENT DOCUMENTS 5,108,416 A * 4/1992 Ryan ...................... A61F 2/958
                                                      604/103.05
5,403,341 A * 4/1995 Solar ......................... A61F 2/86
                                                      606/198

(Continued)

FOREIGN PATENT DOCUMENTS

CN        102858275        1/2013
CN        102892384        1/2013
(Continued)

OTHER PUBLICATIONS

Gurvitch, Ronen et al., "Transcatheter Valve-in-Valve Implantation for Failed Surgical Bioprosthetic Valves," Journal of the American College of Cardiology, vol. 58, No. 21, Sep. 13, 2011, pp. 2196-2209.

(Continued)

*Primary Examiner* — Julian W Woo
(74) *Attorney, Agent, or Firm* — Dicke, Billig & Czaja, PLLC

(57) ABSTRACT

Delivery devices for delivery of a stented prosthetic heart valve. Various delivery devices include an outer sheath assembly including an outer sheath connected to a capsule that is advanced proximally to retain the prosthetic valve, which is secured over an inner shaft assembly of the delivery device. The delivery device further includes a bumper to provide a smooth transition of the capsule over the prosthetic valve during loading and recapture procedures. The bumper is expandable from a first position to a second position in which a distal end of the bumper is expanded to increase its diameter. The bumper can be biased in the second, expanded position so that the bumper automatically transitions to the expanded position upon retraction of the outer sheath.

13 Claims, 3 Drawing Sheets

(58) Field of Classification Search
CPC ...... A61F 2/2418; A61F 2/2436; A61F 2/958;
A61F 2002/9534; A61F 2002/9505; A61F
2002/9528; A61F 2/2427; A61F 2/962;
A61F 2/24
See application file for complete search history.

(56) References Cited

U.S. PATENT DOCUMENTS

| | | | | |
|---|---|---|---|---|
| 5,683,451 | A * | 11/1997 | Lenker | A61F 2/07 606/198 |
| 5,824,041 | A * | 10/1998 | Lenker | A61F 2/07 606/195 |
| 5,895,410 | A * | 4/1999 | Forber | A61B 17/12022 606/191 |
| 5,906,619 | A * | 5/1999 | Olson | A61F 2/95 606/108 |
| 6,254,609 | B1 * | 7/2001 | Vrba | A61F 2/01 606/108 |
| 6,514,280 | B1 * | 2/2003 | Gilson | A61B 17/12031 623/1.11 |
| 6,830,575 | B2 * | 12/2004 | Stenzel | A61F 2/95 606/108 |
| 6,858,034 | B1 * | 2/2005 | Hijlkema | A61F 2/95 606/108 |
| 7,347,868 | B2 * | 3/2008 | Burnett | A61B 17/12099 606/198 |
| 7,918,880 | B2 * | 4/2011 | Austin | A61F 2/95 623/1.11 |
| 8,945,141 | B2 * | 2/2015 | Cahill | A61B 17/3439 606/108 |
| 8,986,362 | B2 * | 3/2015 | Snow | A61F 2/95 606/108 |
| 10,376,363 | B2 * | 8/2019 | Quadri | A61F 2/2436 |
| 2002/0099431 | A1 * | 7/2002 | Armstrong | A61F 2/95 623/1.11 |
| 2003/0114910 | A1 * | 6/2003 | Juhani Laakso | A61F 2/95 623/1.11 |
| 2003/0236545 | A1 * | 12/2003 | Gilson | A61B 17/12031 606/191 |
| 2005/0288764 | A1 * | 12/2005 | Snow | A61F 2/95 623/1.11 |
| 2006/0178726 | A1 * | 8/2006 | Douglas | A61F 2/07 623/1.16 |
| 2006/0184226 | A1 * | 8/2006 | Austin | A61F 2/95 623/1.11 |
| 2006/0276872 | A1 * | 12/2006 | Arbefeuille | A61F 2/07 623/1.11 |
| 2007/0088431 | A1 * | 4/2007 | Bourang | A61F 2/2433 623/2.11 |
| 2007/0129753 | A1 * | 6/2007 | Quinn | A61B 17/0057 606/200 |
| 2007/0270932 | A1 * | 11/2007 | Headley | A61F 2/95 623/1.11 |
| 2008/0015674 | A1 * | 1/2008 | Austin | A61F 2/95 623/1.11 |
| 2008/0255580 | A1 * | 10/2008 | Hoffman | A61F 2/95 606/108 |
| 2009/0093876 | A1 * | 4/2009 | Nitzan | A61F 2/2433 623/2.11 |
| 2010/0049313 | A1 * | 2/2010 | Alon | A61F 2/2418 623/2.11 |
| 2010/0121434 | A1 * | 5/2010 | Paul | A61F 2/24 623/2.11 |
| 2010/0191326 | A1 * | 7/2010 | Alkhatib | A61F 2/013 623/2.11 |
| 2011/0208292 | A1 * | 8/2011 | Von Oepen | A61F 2/97 623/1.23 |
| 2011/0264200 | A1 * | 10/2011 | Tran | A61F 2/2436 623/2.11 |
| 2011/0301702 | A1 * | 12/2011 | Rust | A61F 2/2418 623/2.11 |
| 2013/0211494 | A1 * | 8/2013 | Snow | A61F 2/95 623/1.12 |
| 2015/0112430 | A1 * | 4/2015 | Creaven | A61F 2/2436 623/2.11 |

FOREIGN PATENT DOCUMENTS

| | | |
|---|---|---|
| CN | 105142573 | 12/2015 |
| EP | 2777647 | 9/2014 |
| EP | 2777648 | 9/2014 |
| WO | WO2009/091509 | 7/2009 |
| WO | WO2011/014814 | 2/2011 |
| WO | WO2016/133950 | 8/2016 |

OTHER PUBLICATIONS

PCT/US2017/050339, The International Search Report and the Written Opinion of the International Searching Authority, dated Nov. 21, 2017, 15pgs.

* cited by examiner

STENTED PROSTHETIC HEART VALVE DELIVERY SYSTEM HAVING AN EXPANDABLE BUMPER

BACKGROUND

The disclosure relates to delivery devices for stented prosthetic heart valve loading and implantation. More particularly, the present disclosure provides for delivery devices that prevent a proximal end of the stented prosthetic heart valve from catching or snagging on the delivery device during loading and/or recapture of the stented prosthetic heart valve, for example.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

SUMMARY

The present disclosure relates to numerous delivery devices and methods for stented prosthetic heart valve (hereinafter "prosthetic valve") loading and implantation. Various delivery devices can include an outer sheath assembly, an inner shaft assembly and a handle assembly. The delivery device provides a loaded delivery arrangement in which the prosthetic valve is loaded and compressed over the inner shaft assembly. In some embodiments, compressive tension on the prosthetic valve is variable and adjusted with one or more sutures actuated by the handle assembly. In this way, the delivery device can be manipulated to permit the prosthetic valve to self-expand and partially release from the inner shaft assembly.

When compressed, most stented prosthetic valve designs have a rough outer surface, which can cause damage to the patient during delivery to a native heart valve. Therefore, various embodiments disclosed herein include a delivery device having a protective sheath or capsule covering the outer surface of the prosthetic valve until the prosthetic valve is in position and ready to be deployed. Capsules, however, can snag on a proximal end of the prosthetic valve when the capsule is advanced over the prosthetic valve during loading or recapture of the prosthetic valve within the capsule. In various disclosed embodiments, the delivery device includes a bumper to ease movement of the capsule over the prosthetic valve during loading or recapture procedures. The bumper has a distal end and a proximal end. In a first position, the distal end of the bumper is unrestrained by the delivery device and therefore has a larger, expanded outer diameter as compared to the proximal end due to a natural bias. The expanded distal end provides a ramped surface that provides the smooth transition surface between the capsule and the stented prosthetic heart valve. When the capsule is fully advanced over the prosthetic heart valve, the outer sheath is in a position to completely cover the bumper, thus collapsing the distal end of the bumper against its outward bias so that the bumper is generally shaped like a cylinder. In various embodiments, an expanded diameter of the distal end of the bumper is greater than an inner diameter of the capsule.

In addition to preventing snagging of the capsule during loading and recapture procedures, the disclosed bumpers are advantageous in that a length of the capsule can be reduced. Since the bumper is not positioned within the capsule during delivery, the capsule only needs to be sized to contain the prosthetic valve. A shortened capsule more easily traverses treacherous anatomy such as the aortic arch. The disclosed configurations also allow for a capsule having a lower profile and increased flexibility during delivery of the prosthetic valve as the bumper is housed in the outer sheath.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure is described with reference to preferred embodiments, workers skilled in the art will recognize that changes can be made in form and detail without departing from the spirit and scope of the present disclosure.

Figure 1:
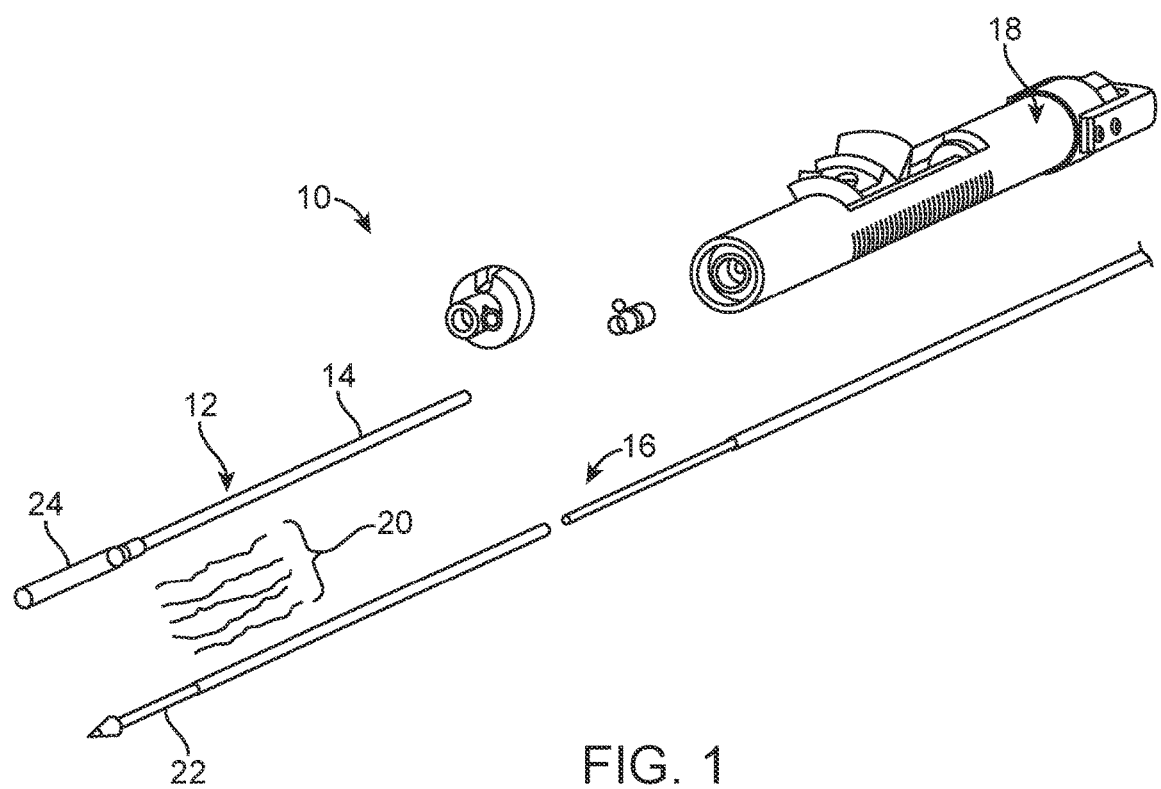
FIG. 1 is a perspective view of an example of a delivery device for delivering a stented prosthetic heart valve.
Figure 2A:
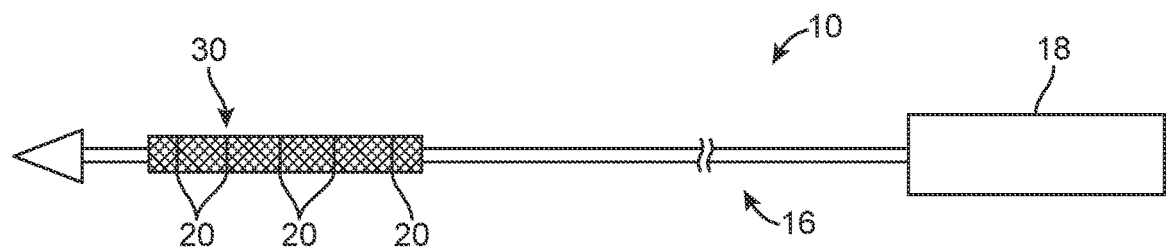
FIG. 2A is a schematic illustration of the delivery device of FIG. 1 having the stented prosthetic heart valve positioned over an inner shaft assembly of the delivery device with a plurality of sutures in a compressed arrangement.
Figure 2B:
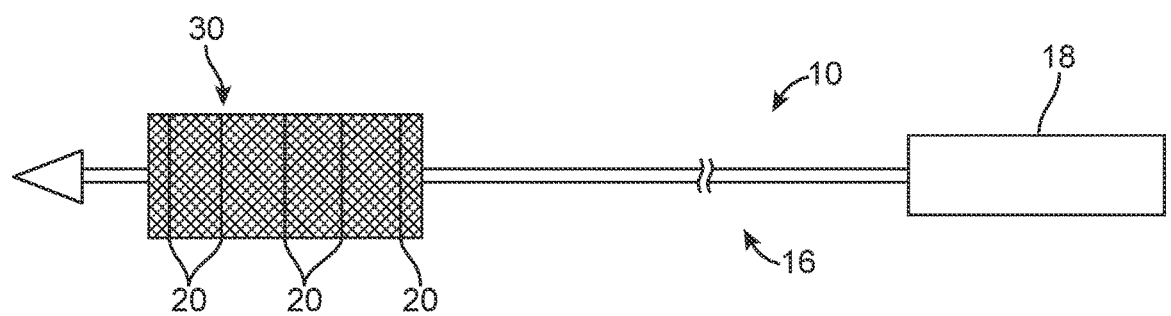
FIG. 2B is a partial, schematic illustration of the delivery device of FIG. 2A having the stented prosthetic heart valve positioned over the inner shaft assembly; the stented prosthetic heart valve shown in an expanded arrangement.

As described below, some aspects of the present disclosure relate to transcatheter stented prosthetic heart valve delivery devices utilizing one or more sutures to retain the stented prosthetic heart valve during delivery to a target site. By way of background, general components of one non-limiting example of a delivery device 10 with which some embodiments of the present disclosure are useful are illustrated in FIGS. 1-2B. The delivery device 10 is arranged and configured for percutaneously delivering a stented prosthetic heart valve 30 (schematically illustrated, hereinafter "prosthetic valve") to a patient's native defective heart valve. The delivery device 10 includes an outer sheath assembly 12 having an outer sheath 14, an inner shaft assembly 16 and a handle assembly 18. One or more sutures 20 are provided, and can be considered part of the delivery device 10 in some embodiments or as part of the prosthetic valve 30 in other embodiments. The delivery device 10 provides a loaded, compressed arrangement (FIG. 2A) in which the prosthetic valve 30 is loaded over the inner shaft assembly 16 and is compressively retained on a spindle 22 by the sutures 20. As is schematically illustrated in FIGS. 2A-2B, compression on the prosthetic valve 30 is adjustable with the one or more sutures 20. Once loaded and compressed, the prosthetic valve 30 is delivered to the native defective heart valve. Once in position, tension in the sutures 20 is lessened or released to permit the prosthetic valve 30 to self-expand to an expanded arrangement, partially releasing and ultimately fully deploying the prosthetic valve 30 from the inner shaft assembly 16 (see, FIG. 2B). In this embodiment, the outer sheath 14 is interconnected to a capsule 24 that is selectively disposed over the prosthetic valve 30 that assists in constraining the prosthetic valve 30 in the compressed arrangement and can be retracted by the handle assembly 18 to expose the prosthetic valve 30. The present disclosure focuses on numerous ways to incorporate at least one bumper into a delivery device, such as the delivery device 10. As will be discussed in detail below, the disclosed bumpers are arranged and configured to prevent the capsule 24 from snagging on the prosthetic valve 30 during loading and recapture procedures.

As referred to herein, stented prosthetic heart valves or "prosthetic valves" useful with the various devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The prosthetic valves of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 3A:
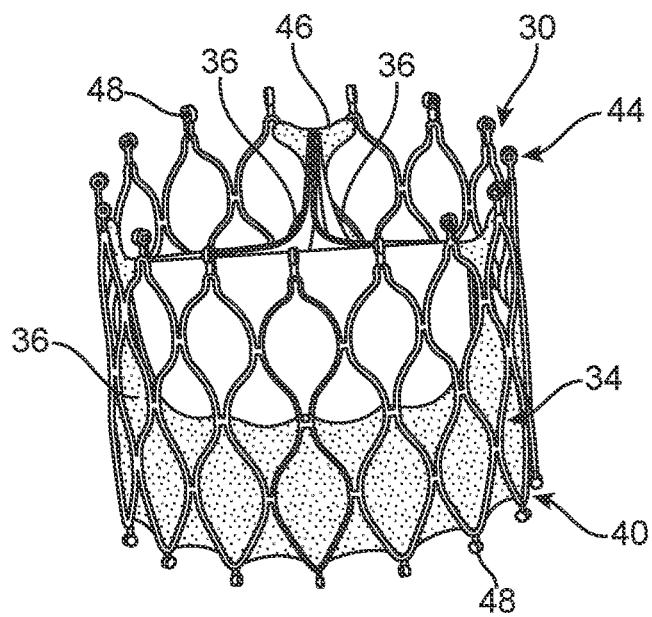
FIG. 3A is a perspective view of the stented prosthetic heart valve that can be used with the delivery devices disclosed herein shown in the expanded arrangement.
Figure 3B:
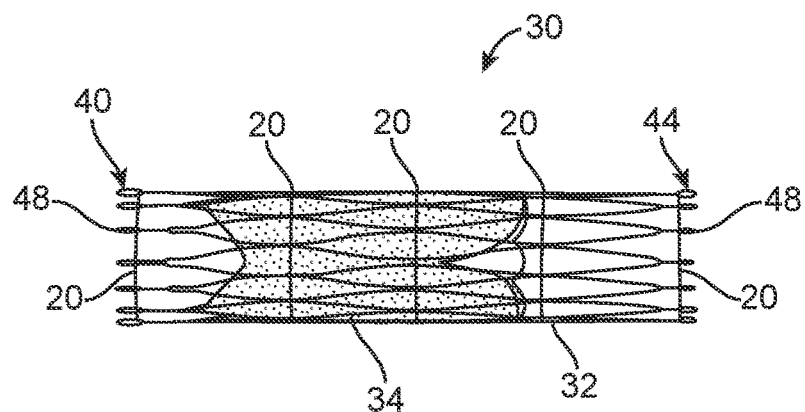
FIG. 3B is a front view of the stented prosthetic heart valve of FIG. 3A in the compressed arrangement.

The non-limiting example of the stented prosthetic valve 30 is illustrated in detail in FIGS. 3A-3B. As a point of reference, the prosthetic valve 30 is shown in a normal or expanded arrangement in the view of FIG. 3A and a compressed arrangement in FIG. 3B. The prosthetic valve 30 includes a stent or stent frame 32 and a valve structure 34. The stent frame 32 can assume any of the forms mentioned above, and is generally constructed to be self-expandable from the compressed arrangement to the normal, expanded arrangement. As discussed above, compression of the prosthetic valve 30 can be achieved with one or more sutures 20.

The valve structure 34 of the prosthetic valve 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some prosthetic valve constructions, such as that of FIGS. 3A-3B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The prosthetic valve 30 includes a first end 40 and an opposing second end 44 of the prosthetic valve 30. As shown, the stent frame 32 can have a lattice or cell-like structure, and optionally forms or provides posts 46 corresponding with commissures of the valve structure 34 as well as features 48 (e.g. crowns, eyelets or other shapes) at the first and second ends 40, 44. If provided, the posts 46 are spaced equally around frame 32 (only one post 46 is clearly visible in FIG. 3A).

Figure 4A:
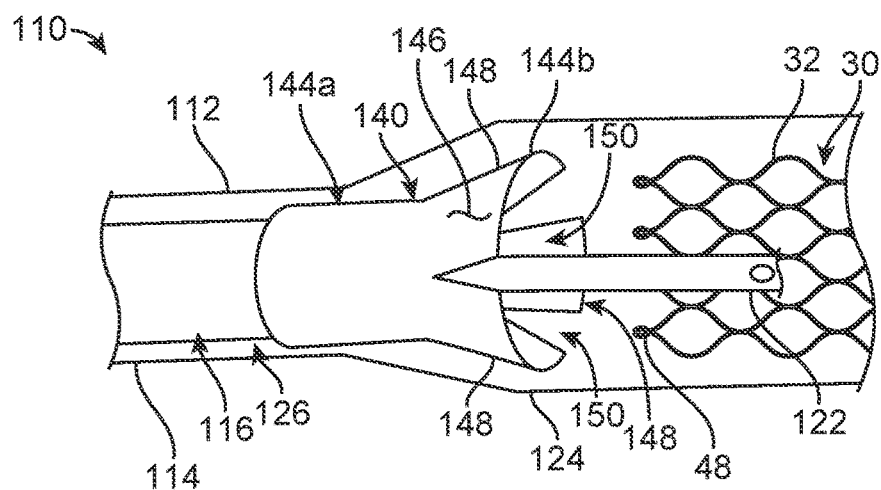
FIG. 4A is a partial, schematic view of a delivery device largely similar to that of FIGS. 1-2B including a bumper in a first, expanded position; wherein various elements are shown as transparent for clarity.
Figure 4B:
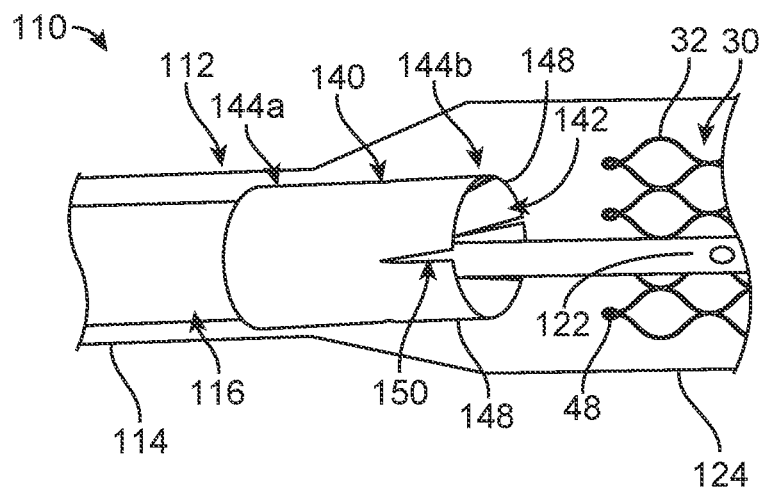
FIG. 4B is a partial, schematic view of the delivery device of FIG. 4A showing the bumper in a second, collapsed position; wherein various elements are shown as transparent for clarity.

FIGS. 4A-4B schematically illustrate select components of a delivery device 110 that is largely similar to that of FIGS. 1-2B except as explicitly stated. The delivery device 110 includes an outer sheath assembly 112 having an outer sheath 114, an inner shaft assembly 116, and can further include a handle assembly (such as handle assembly 18 of FIG. 1). In this embodiment, the delivery device 110 includes a bumper 140 defining a cavity 142. The bumper 140 is positioned over the inner shaft assembly 116 and maintained in place via adhesive bonding or the like. The bumper 140 further has a proximal end 144a and a distal end 144b. The distal end 144b is configured to transition between a first expanded position, in which the distal end 144b flares out with respect to the proximal end 114a to create a ramped surface 146 (FIG. 4A), to a second position in which the bumper 140 is generally cylindrical (i.e. the surface 146 no longer forms the ramped surface 146) and fits entirely within the outer sheath 114 (FIG. 4B). In this particular embodiment, expansion of distal end 144b is facilitated with a plurality of petals 148 separated by a plurality of cuts or slits 150. The petals 148 are configured to be biased in the expanded position of FIG. 4A. The bumper 140, or at least the distal end 144b of the bumper 140, can be made of a shape-memory material such as Nitinol™, which can provides the self-biasing capability. The bumper 140 can include three petals 148, as shown, or another number of petals. Although shown as a unitary structure, the bumper 140 can be constructed of a plurality of assembled components in alternate embodiments.

The delivery device 110 is further configured to translate between two positions for positioning a capsule 124 of the outer sheath assembly 112 with respect to the prosthetic valve 30 (the outer sheath assembly 112 is shown as transparent for ease of illustration). The capsule 124 covers the prosthetic valve 30 during delivery so that the stent frame 32 (schematically shown) does not scrape the patient's anatomy. In the state of FIG. 4A, the capsule 124 and outer sheath 114 are positioned with respect to the inner shaft assembly 116 to provide a loading or recapture state in which the distal end 144b of the bumper 140 expands in diameter to form the ramped surface 146 that provides for a smooth transition as the capsule 124 moves over the proximal end (either end 40 or 44 of the stent frame 32) of the prosthetic valve 30 for loading or recapture of the valve 30. In this embodiment, the bumper 140 expands when petals 148 flare outwardly with respect to the proximal end 144a of the bumper 140. In various embodiments, the distal end 144b is configured such that at least a greatest diameter of the distal end 144b is larger than an inner diameter of the capsule 124. In the state of FIG. 4B, the valve 30 is loaded into the capsule 124 and the outer sheath 114 is positioned entirely over the bumper 140 to compress the distal end 144b against its outward bias. In the configuration of FIG. 4B, the bumper 140 is generally cylindrical, fitting entirely within an interior 126 of the outer sheath 114 and therefore provides an advantage as this configuration does not increase the profile of the delivery device 110.

To initially load the prosthetic valve 30 into the capsule 124 of the delivery device 110, the bumper 140 can be positioned as is generally shown in FIG. 4A by positioning the outer sheath 114 such that it is proximal the distal end 144b of the bumper 140. In this position, the bumper 140 is freed from the confines of the outer sheath 114 so that it naturally expands to the position in FIG. 4A, thus creating the ramped surface 146. The outer sheath assembly 112 is then advanced distally over the ramped surface 146, past the distal end 144b of the bumper 140 and over the prosthetic valve 30 without snagging or catching on the prosthetic valve 30. Once loaded within the capsule 124, the outer sheath assembly 112 is configured so that the outer sheath 114 will be positioned over and compress the bumper 140 against its natural bias to reduce the profile of the bumper 140 for the delivery step. At this stage as shown in FIG. 4B, the prosthetic valve 30 is sheathed and ready for delivery. Once the prosthetic valve 30 is delivered to a target site and ready to be deployed, the outer sheath assembly 112 is retracted to unsheathe the capsule 124 from the prosthetic valve 30. As the outer sheath assembly 112 is retracted, the bumper 140 naturally expands at the distal end 144b once released from the confines of the outer sheath 114 and the petals 148 once again form the ramped surface 146. If recapture of the prosthetic valve 30 within the capsule 124 is desired, the ramped surface 146 again provides a smooth transition surface for the capsule 124 to travel across as it moves distally over the bumper 140 and the prosthetic valve 30. After the capsule 124 is later retracted, tension in each suture (not shown, see also the disclosure relating to FIGS. 2A-2B) is lessened or released to permit the prosthetic valve 30 to self-expand, partially releasing and ultimately fully deploying the prosthetic valve 30 from a spindle 122 of the inner shaft assembly 116. Next, each suture is released from the prosthetic valve 30 and withdrawn from the patient along with the delivery device 110.

Figure 5:
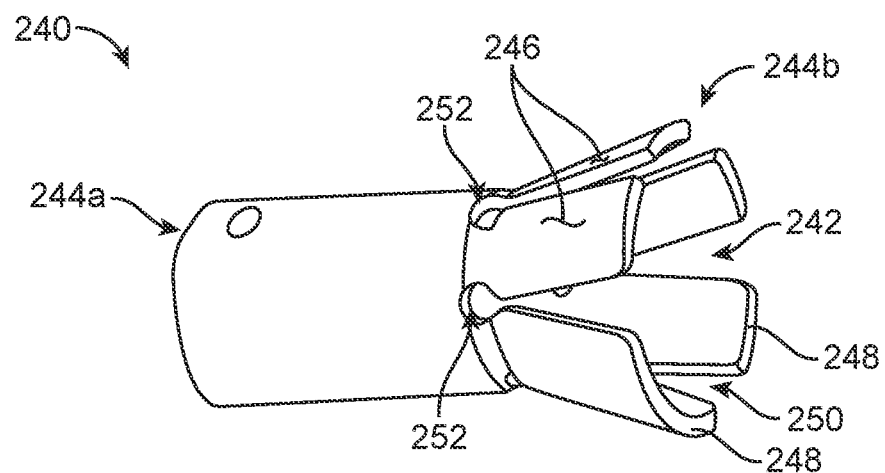
FIG. 5 is a perspective view of an alternate bumper for use with delivery devices similar to those illustrated in FIGS. 1-2B and 4A-4B.

One alternative bumper 240, largely similar to the bumper 140 of FIGS. 4A-4B, is shown in FIG. 5. The bumper 240 defines a cavity 242 and has opposing proximal and distal ends 244a, 244b. As with the prior embodiment, the distal end 244b is configured to have a natural outward bias to the position illustrated in FIG. 5. In this position, the distal end 244b is configured such that at least a greatest diameter of the distal end 244b can be larger than an inner diameter of the capsule (not shown, see also the disclosure relating to FIGS. 1 and 4A-4B). In this embodiment, the distal end 244b includes a plurality of petals 248 pivotally connected to the proximal end 244a and defined by slits or cuts 250 in the distal end 244b (only a few of the petals 248 and slits 250 are labeled for ease of illustration). The slits 250 may terminate at a circular aperture 252 designed to ease pivotal movement of the petals 248. The plurality of petals 248, when in the expanded position, collectively define a ramped surface 246 to provide a smooth transition as the capsule is advanced over the compressed prosthetic valve (see also, the disclosure relating to FIGS. 4A-4B). The bumper 240 can include three petals 248 as shown in the embodiment of FIGS. 4A-4B, six petals as is shown in the embodiment of FIG. 5 or another number of petals. When positioned inside the outer sheath 114 of the delivery device 110, the petals 248 are forced into a collapsed position so that the bumper 240 has a generally cylindrical configuration similar to what is shown in FIG. 4B with respect to bumper 140. Although shown as a unitary structure, the bumper 240 can be constructed of a plurality of pieces in alternate embodiments. As with the prior embodiment, the bumper 240 can be made of a shape-memory material or the like. Use of a delivery device having the bumper 240 is generally the same as use of the delivery device 110 having the bumper 140 of FIGS. 4A-4B).

In addition to preventing snagging of the capsule during loading and recapture procedures, the disclosed bumpers are advantageous in that the capsule length can be reduced. Since the bumper is not positioned within the capsule during delivery, the capsule only needs to be long enough to contain the prosthetic valve. A shortened capsule more easily traverses treacherous anatomy such as the aortic arch. The disclosed configurations also provide for a capsule having a lower profile and increased flexibility during delivery of the prosthetic valve as the bumper is housed in the outer sheath.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthetic heart valve to a native heart valve; the delivery device comprising:

an inner shaft assembly configured to retain the stented prosthetic heart valve;

a bumper secured to the inner shaft assembly so that the inner shaft assembly extends through a cavity defined by the bumper, the bumper having a distal end, a proximal end and an outer surface; wherein the bumper has a compressed position and an expanded position; wherein the distal end of the bumper is made of a shape memory metal to bias the distal end in the expanded position; and an outer sheath assembly slidably positioned over at least part of the inner shaft assembly, the outer sheath assembly including an outer sheath terminating at a capsule, the outer sheath positioned proximal with respect to the capsule, the capsule configured to selectively cover the stented prosthetic heart valve; the capsule configured to slide distally and proximally over the bumper to sheathe the stented prosthetic heart valve; wherein, in a delivery position, the outer sheath compresses the distal end of the bumper and the bumper is not positioned within the capsule; wherein, in a retracted position, the outer sheath is positioned proximal with respect to the distal end of the bumper and the capsule covers the bumper.

2. The delivery device of claim 1, when in the expanded position, the outer surface further includes a ramped surface having an increasing outer diameter.

3. The delivery device of claim 1, wherein the capsule has an inner diameter and further wherein a greatest outer diameter of the distal end of the bumper in the expanded position is larger than the inner diameter of the capsule.

4. The delivery device of claim 1, wherein the distal end of the bumper includes a plurality of longitudinally extending cuts.

5. The delivery device of claim 4, wherein the distal end of the bumper includes a plurality of petals separated by the cuts.

6. The delivery device of claim 5, wherein the petals are pivotable about the proximal end of the bumper.

7. The delivery device of claim 1, wherein in the compressed position, the bumper is generally cylindrical.

8. The delivery device of claim 1, wherein the bumper is constructed of a unitary piece of material.

9. The delivery device of claim 1, wherein the bumper is fixed to the inner shaft assembly to maintain a longitudinal position of the bumper with respect to the inner shaft assembly.

10. The delivery device of claim 1, wherein the bumper includes a plurality of slits and an aperture at a proximal end of each slit.

11. The delivery device of claim 1, the expanded position being one in which a distal end of the bumper flares outwardly with respect to the proximal end.

12. A delivery device for delivering a stented prosthetic heart valve to a native heart valve; the delivery device comprising:

an inner shaft assembly configured to retain the stented prosthetic heart valve;

a bumper secured to the inner shaft assembly so that the inner shaft assembly extends through a cavity defined by the bumper, the bumper having a distal end, a proximal end and an outer surface; wherein the bumper has a compressed position and an expanded position; wherein the distal end of the bumper is made of a shape memory metal to bias the distal end in the expanded position; and an outer sheath assembly slidably positioned over at least part of the inner shaft assembly, the outer sheath assembly including an outer sheath terminating at a capsule, the outer sheath having an inner diameter that is smaller than an inner diameter of the capsule, the outer sheath positioned proximal with respect to the capsule, the capsule configured to selectively cover the stented prosthetic heart valve; the capsule configured to slide distally and proximally over the bumper to sheathe the stented prosthetic heart valve; wherein, in a delivery position, the outer sheath compresses the distal end of the bumper; wherein, in the expanded position, the distal end of the bumper has a maximum diameter that is greater than the inner diameter of the capsule.

13. The delivery device of claim 12, wherein, in the delivery position, the bumper is not positioned within the capsule.

* * * * *